United States Patent
Higuchi

(10) Patent No.: US 7,501,816 B2
(45) Date of Patent: Mar. 10, 2009

(54) FLAW DETECTION METHOD AND FLAW DETECTION APPARATUS

(75) Inventor: Sadao Higuchi, Komae (JP)

(73) Assignee: Central Research Institute Of Electric Power Industry, Tokyo (JP)

( * ) Notice: Subject to any disclaimer, the term of this patent is extended or adjusted under 35 U.S.C. 154(b) by 143 days.

(21) Appl. No.: 11/315,145

(22) Filed: Dec. 23, 2005

(65) Prior Publication Data
US 2006/0152216 A1 Jul. 13, 2006

(30) Foreign Application Priority Data
Jan. 7, 2005 (JP) ............................ 2005-002140
Nov. 4, 2005 (JP) ............................ 2005-320723

(51) Int. Cl.
*G01R 33/02* (2006.01)

(52) U.S. Cl. .................... 324/244.1; 324/258; 324/260; 348/359; 359/280

(58) Field of Classification Search ................ 324/237, 324/238, 258, 260, 228, 216, 244.1; 348/359; 359/280
See application file for complete search history.

(56) References Cited

U.S. PATENT DOCUMENTS

| | | | | |
|---|---|---|---|---|
| 3,315,160 A | * | 4/1967 | Goodman | 714/735 |
| 4,516,073 A | * | 5/1985 | Doriath et al. | 324/244.1 |
| 4,563,646 A | * | 1/1986 | Desormiere | 324/244.1 |
| 4,625,167 A | * | 11/1986 | Fitzpatrick | 324/235 |
| 4,931,635 A | * | 6/1990 | Toyama | 250/225 |
| 5,574,368 A | * | 11/1996 | Horn et al. | 324/228 |
| 6,462,539 B2 | * | 10/2002 | Moriya et al. | 324/244.1 |
| 6,534,977 B1 | * | 3/2003 | Duncan et al. | 324/244.1 |
| 6,784,662 B2 | * | 8/2004 | Schlicker et al. | 324/242 |
| 2005/0146324 A1 | * | 7/2005 | Goldfine et al. | 324/238 |

FOREIGN PATENT DOCUMENTS

JP 2-189457 A 7/1990
JP 6-294773 A 10/1994

OTHER PUBLICATIONS

Martindale, Heath, & Easton "Fundamentals of Physics: A Senior Course"; 1986; D.C. Heath Canada Ltd.; p. 414.*
Martindale, Heath, & Easton "Fundamentals of Physics: A Senior Course"; 1986; D.C. Heath Canada Ltd.; p. 414.*

* cited by examiner

*Primary Examiner*—W. B. Perkey
*Assistant Examiner*—Michael A Strieb
(74) *Attorney, Agent, or Firm*—Sughrue Mion, PLLC

(57) ABSTRACT

A flaw detection apparatus includes a coil for producing an alternating-current magnetic field for flowing eddy currents in a magnetic material; a magneto-optical element disposed at the center of an inner peripheral portion of the coil and having a reflective film at an end face thereof opposed to the face of the member to be flaw-detected; an optical fiber for entering light from a light source into the magneto-optical element toward the reflective film via a circulator; an optical fiber for entering reflected light reflected by the reflective film into an analyzer via the circulator; a photoelectric conversion element for converting output light of the analyzer into an electrical signal; and a computing device for processing an output signal of the photoelectric conversion element and detecting a flaw of the member to be flaw-detected, based on the rotation angle of the plane of polarization of the reflected light.

26 Claims, 18 Drawing Sheets

Direction of inspection

Direction of inspection

RELATED ART

RELATED ART

FLAW DETECTION METHOD AND FLAW DETECTION APPARATUS

BACKGROUND OF THE INVENTION

1. Field of the Invention

This invention relates to a flaw detection method and a flaw detection apparatus. More particularly, the invention relates to those useful when applied in making a nondestructive inspection of a member, which is a magnetic material and is a subject for flaw detection, by generating eddy currents in the member by an alternating magnetic field generated by a coil, and examining a change in a magnetic flux density due to the eddy currents disturbed by the presence of a flaw.

2. Description of the Related Art

The eddy-current flaw detection method is known as a flaw detection method which detects a flaw on the surface or in the interior of a metallic material used in a component of electric power equipment (for example, a gas turbine blade of thermal power generating system). This eddy-current flaw detection method detects a flaw by generating eddy currents in a member as a subject for flaw detection (hereinafter referred to as a member to be flaw-detected) by an alternating magnetic field generated by a coil, and detecting a change in a magnetic flux density due to the eddy currents disturbed by the presence of the flaw.

The above-mentioned flaw detection method will be described in further detail with reference to FIGS. 20A to 20D showing the principle of this method. As shown in FIG. 20A, a magnetic flux 03 is generated by flowing an electric current 02 through a coil 01. Then, as shown in FIG. 20B, the coil 01 is approached by a member 04 to be flaw-detected, which is a magnetic material, to generate eddy currents 05 in this member 04 to be flaw-detected. As a result, a magnetic flux 06 due to the eddy currents 05 is generated, as shown in FIG. 20C. If, at this time, a flaw 07 exists in the member 04 to be flaw-detected, as shown in FIG. 20D, the eddy currents 05 are disturbed. Consequently, the magnetic flux 06 by the eddy currents 05 changes. Based on such a change in the magnetic flux 06, the flaw 07 of the member 04 to be flaw-detected is detected.

In recent years, however, a further improvement in flaw detection accuracy has been desired. The accuracy of the eddy-current flaw detection method according to the earlier technology has proved insufficient, particularly when identifying the location of the flaw.

A proposal has been made for a flaw detection method which detects a flaw in a member to be flaw-detected, which is a magnetic material, by detecting a change in a magnetic flux density as a change in the rotation angle of the plane of polarization with the use of Faraday effect (a phenomenon in which when linearly polarized light passes through a magnetized crystal, the plane of polarization rotates). An example is the flaw detection method disclosed in Japanese Patent Application Laid-Open No. 1990-189457.

According to this flaw detection method, as shown in FIGS. 21 and 22, a magnetic field is imparted by a magnetization means 013 to a portion, including a test surface 012, of a test sample 011 comprising a magnetic material. In this state, the one of the test sample 011 and a sensor-unit 015, which is disposed in the vicinity of the test sample 011 and incorporates a Faraday element 016, is moved. Simultaneously, light L is enters the Faraday element 016, and the optical intensity of the light L, which exits from the Faraday element 016, is measured to detect fluctuations in a magnetic flux leakage A from the test sample 011, thereby detecting a defect region 014 of the test sample 011. The sensor unit 015 integrally accommodates a polarizer 017, an analyzer 018, and a mirror 019, as well as the Faraday element 016, inside a housing.

Thus, the light L emitted from an optical transmitter 020 arrives at the polarizer 017 via an input optical fiber 021, reaches the outside of the sensor unit 015 via the Faraday element 016, the analyzer 018 and the mirror 019, and becomes incident on an optical receiver 023 via an exit optical fiber 022. The light L incident on the optical receiver 023 is converted into an electrical signal θ, and processed in a predetermined manner by a computing unit 024, whereafter the result of processing is indicated on a display unit 025 such as an X-Y recorder.

According to the above-described flaw detection method, however, the light L, which has been incident on the Faraday element 016 via the polarizer 017, crosses the Faraday element 016 and enters the analyzer 018. Thus, the light L is influenced by the magnetic field in the entire region, beginning at the site of its entry into the Faraday element 016 and ending at the site of its departure from the Faraday element 016. Accordingly, the region for measurement of the magnetic flux density widens, resulting in poor resolution.

As documents on publicly known technologies relevant to the present invention, the aforementioned laid-open patent application and Japanese Patent Application Laid-Open No. 1994-294773 can be named.

The present invention has been accomplished in light of the above-described problems with the earlier technologies. It is an object of the present invention to provide a flaw detection method and a flaw detection apparatus which are applied when detecting a flaw in a magnetic material, as a member to be flaw-detected, by detecting a change in a magnetic flux density as a change in the rotation angle of the plane of polarization with the use of Faraday effect, and which can impart high resolution to a measurement region for magnetic flux density to achieve flaw detection with high accuracy.

SUMMARY OF THE INVENTION

The present invention, aimed at attaining the above-mentioned object, is based on the following findings:

(1) An example of calculation of a change in a magnetic flux density caused by a flaw in a magnetic material, as a member to be flaw-detected, will be offered. Assume that the frequency of an alternating voltage applied to a coil 1 as shown in FIG. 1 is 500 kHz, an electric current value is 1 AT, and the distance between the coil 1 and a member to be flaw-detected, 2, is 0.5 mm. In this case, the magnetic flux density Bo of a magnetic flux occurring from the coil 1 is 4.1739 G, and a magnetic flux density change ΔB due to a flaw 0.2 mm deep formed in the member 2 to be flaw-detected is 10 mG. By repeating the same calculation, it becomes possible to obtain the value of the magnetic flux density change ΔB in accordance with the depth d of the flaw.

This suggests that if the relationship between the depth d of the flaw and the magnetic flux density change ΔB is found under certain conditions, and this relationship is stored as a database, then the depth d of the flaw can be obtained by referring to this database in comparison with data from measurements.

At this time, a magneto-optical element 3 is located at the central position of an inner peripheral circle formed by the coil 1. By so doing, light incident on the magneto-optical element 3 has its plane of polarization rotated by Faraday effect. Thus, light is entered into the magneto-optical element 3 by an optical fiber 4 with a small core diameter, and reflected light reflected by an end face of the magneto-optical element 3 is withdrawn to detect the rotation amount of the plane of polarization, whereby a change in the magnetic flux density can be detected with high resolution. This is because the resolution depends on the diameter of the optical fiber 4. A single-mode optical fiber, preferred for such applications, is available with a core diameter of 10 μm.

(2) FIG. 2 is an explanatory drawing conceptually showing the manner of flaw detection for various types of flaws formed in a member to be flaw-detected. As shown in this drawing, a penetrating flaw was formed in a member 2a to be flaw-detected, a crack was formed in the face of a member 2b to be flaw-detected, and a crack was formed in the back of a member 2c to be flaw-detected. FIGS. 3 to 5 are characteristic views showing the results of flaw detection performed for the members 2a to 2c to be flaw-detected, in this sequence. That is, the rotations of the plane of polarization by the magnetic flux, which were detected via the optical fiber 4, were detected as voltage signals representing these rotations. The respective drawings show the measurements of magnetic fields in different parts made when the coil 1 and the magneto-optical element 3 were moved along the surfaces of the members 2a to 2c to be flaw-detected. The phase indicated therein refers to a phase difference between the voltage signals representing the magnetic field produced by the coil 1 and the magnetic field detected by the magneto-optical element 3.

Reference to FIGS. 3 to 5 reveals differences among the shapes of the resulting signals according to the properties of the respective flaws, and shows that the flaws are present in the vicinity of the maximum values of the output voltages.

These facts suggest that a database specifying the state of the flaw can be constructed by accumulating such data.

(3) FIG. 6 is a view showing characteristics obtained by generating a magnetic field, in a flaw-free member 2 to be flaw-detected, by the coil 1, and investigating a measurable magnetic field, as a study of the sensitivity of the magneto-optical element 3. A magnetic flux density applied was 4 G, the frequency of an applied voltage was 100 kHz, a resolution band width was 10 Hz, and 20 measurements were averaged. The measurement results obtained under these conditions were a signal strength of −45.75 dBm, a noise level of −105.81 dBm, an SNR of 60.16 dB, and a noise equivalent magnetic field of 4G/1007=4.04 mG. That is, measurement can be made for 4.04 mG or more. This suggests that a flaw showing 10 mG, which is the result of calculation in the aforementioned paragraph (1), can be sufficiently measured.

A first aspect of the present invention based on the above findings is a flaw detection method, comprising:

generating eddy currents in a magnetic material, as a member to be flaw-detected, by an alternating-current magnetic field produced by a coil;

having light enter a magneto-optical element, disposed in a magnetic field formed by the eddy currents, with the use of an optical fiber, and reflecting the light by an end face of the magneto-optical element to withdraw the reflected light; and detecting a change in a magnetic flux density due to a flaw of the member to be flaw-detected, based on an rotation angle of a plane of polarization of the reflected light by Faraday effect to perform flaw detection of the member to be flaw-detected.

A second aspect of the invention is a flaw detection apparatus, comprising:

a coil for producing an alternating-current magnetic field for flowing eddy currents in a magnetic material as a member to be flaw-detected;

a magneto-optical element disposed in a neighborhood of the coil and having an end face provided with a reflective film;

an incidence optical fiber for entering light from a light source into the magneto-optical element toward the reflective film;

an exit optical fiber for entering reflected light reflected by the reflective film into an analyzer;

a photoelectric conversion element for converting output light of the analyzer into an electrical signal; and computing means for processing an output signal of the photoelectric conversion element and detecting a flaw of the member to be flaw-detected, based on a rotation angle of a plane of polarization of the reflected light.

A third aspect of the invention is the flaw detection apparatus according to the second aspect, wherein the incidence optical fiber and the exit optical fiber are formed of a single optical fiber, a circulator is interposed halfway through an optical path of the single optical fiber, the light from the light source enters the magneto-optical element via the circulator, and the reflected light from the magneto-optical element enters the analyzer via the circulator.

A fourth aspect of the invention is the flaw detection apparatus according to the second aspect, wherein a polarizer, which adjusts the output light from the optical fiber to become linearly polarized light at a position of the analyzer, is disposed halfway through the optical path formed of the optical fiber.

A fifth aspect of the invention is the flaw detection apparatus according to the second aspect, wherein the optical fiber is formed of a polarization maintenance fiber.

A sixth aspect of the invention is the flaw detection apparatus according to the second aspect, wherein a reflecting surface formed by the reflective film is rendered as a curved surface so that the reflected light is converged on an end plane of incidence of the exit optical fiber.

A seventh aspect of the invention is a flaw detection apparatus, comprising:

a coil for producing an alternating-current magnetic field for flowing eddy currents in a magnetic material as a member to be flaw-detected;

a magneto-optical element disposed in a neighborhood of the coil and having an end face provided with a reflective film;

two lines of incidence optical fibers for entering light from light sources into the magneto-optical element toward the reflective film;

two lines of exit optical fibers for entering reflected light reflected by the reflective film into analyzers;

photoelectric conversion elements for converting output lights of the analyzers into electrical signals; and computing means for processing output signals of the photoelectric conversion elements and detecting a flaw of the member to be flaw-detected, based on rotation angles of planes of polarization of the reflected lights.

An eighth aspect of the invention is the flaw detection apparatus according to the seventh aspect, wherein each of the incidence optical fibers and each of the exit optical fibers are formed of single optical fibers, a circulator is interposed halfway through an optical path of each of the single optical fibers, the light from each of the light sources enters the magneto-optical element via each of the circulators, and the reflected lights from the magneto-optical element enter into the analyzers via the circulators.

A ninth aspect of the invention is the flaw detection apparatus according to the seventh aspect, wherein a polarizer, which adjusts the output light from each of the optical fibers to become linearly polarized light at a position of each of the analyzers, is disposed halfway through each of the optical paths formed of each of the optical fibers.

A tenth aspect of the invention is the flaw detection apparatus according to the seventh aspect, wherein each of the optical fibers is formed of a polarization maintenance fiber.

An eleventh aspect of the invention is the flaw detection apparatus according to the seventh aspect, wherein a reflecting surface formed by the reflective film is rendered a curved surface so that each of the reflected lights is converged on an end plane of incidence of each of the exit optical fibers.

A twelfth aspect of the invention is the flaw detection apparatus according to the second aspect, wherein the magneto-optical element is disposed at a center of an inner peripheral portion of the coil.

A thirteenth aspect of the invention is the flaw detection apparatus according to the second aspect, wherein the magneto-optical element is disposed in contact with a circumferential surface of the coil.

A fourteenth aspect of the invention is the flaw detection apparatus according to the second aspect, wherein the magneto-optical element is disposed a third of a distance spaced from an inner peripheral surface of the coil, the distance being from the inner peripheral surface of the coil to a center of an inner peripheral portion of the coil.

A fifteenth aspect of the invention is the flaw detection apparatus according to the second aspect, wherein a plurality of the magneto-optical elements are also disposed in an outer peripheral portion of the coil so that flaw detection at sites where the magneto-optical elements are disposed can also be performed simultaneously.

A sixteenth aspect of the invention is the flaw detection apparatus according to the second aspect, wherein a plurality of the magneto-optical elements are disposed in an inner peripheral portion of the coil so that flaw detection at sites where the magneto-optical elements are disposed can be performed simultaneously.

A seventeenth aspect of the invention is the flaw detection apparatus according to the second aspect, further comprising two of the coils each having the magneto-optical element disposed in an inner peripheral portion thereof, and wherein electric currents in opposite directions are fed to the coils so that magnetic fluxes generated by the coils are superimposed on each other, and another magneto-optical element is disposed between one of the coils and other of the coils so that flaw detection can be performed based on a rotation angle of a plane of polarization due to the superimposed magnetic fluxes.

An eighteenth aspect of the invention is the flaw detection apparatus according to the second aspect, wherein in order that the magneto-optical element can detect a change in a magnetic field of a component in a direction parallel to a face of the member to be flaw-detected, light is entered in the parallel direction, and the light is reflected in the parallel direction by the reflective film formed on a surface perpendicular to the parallel direction.

A nineteenth aspect of the invention is the flaw detection apparatus according to the second aspect, wherein the coil is rectangularly shaped, and the magneto-optical element is disposed in proximity to a straight-line portion of the coil.

A twentieth aspect of the invention is the flaw detection apparatus according to the seventh aspect, wherein the magneto-optical element is disposed at a center of an inner peripheral portion of the coil.

A twenty-first aspect of the invention is the flaw detection apparatus according to the seventh aspect, wherein the magneto-optical element is disposed in contact with a circumferential surface of the coil.

A twenty-second aspect of the invention is the flaw detection apparatus according to the seventh aspect, wherein the magneto-optical element is disposed a third of a distance spaced from an inner peripheral surface of the coil, the distance being from the inner peripheral surface of the coil to a center of an inner peripheral portion of the coil.

A twenty-third aspect of the invention is the flaw detection apparatus according to the seventh aspect, wherein a plurality of the magneto-optical elements are also disposed in an outer peripheral portion of the coil so that flaw detection at sites where the magneto-optical elements are disposed can also be performed simultaneously.

A twenty-forth aspect of the invention is the flaw detection apparatus according to the seventh aspect, wherein a plurality of the magneto-optical elements are disposed in an inner peripheral portion of the coil so that flaw detection at sites where the magneto-optical elements are disposed can be performed simultaneously.

A twenty-fifth aspect of the invention is the flaw detection apparatus according to the seventh aspect, further comprising two of the coils each having the magneto-optical element disposed in an inner peripheral portion thereof, and wherein electric currents in opposite directions are fed to the coils so that magnetic fluxes generated by the coils are superimposed on each other, and another magneto-optical element is disposed between one of the coils and other of the coils so that flaw detection can be performed based on a rotation angle of a plane of polarization due to the superimposed magnetic fluxes.

An twenty-sixth aspect of the invention is the flaw detection apparatus according to the seventh aspect, wherein in order that the magneto-optical element can detect a change in a magnetic field of a component in a direction parallel to a face of the member to be flaw-detected, light is entered in the parallel direction, and the light is reflected in the parallel direction by the reflective film formed on a surface perpendicular to the parallel direction.

A twenty-seventh aspect of the invention is the flaw detection apparatus according to the seventh aspect, wherein the coil is rectangularly shaped, and the magneto-optical element is disposed in proximity to a straight-line portion of the coil.

According to the above-described features of the present invention, resolution for flaw detection based on the rotation of the plane of polarization with the use of Faraday effect is defined by the core diameter of an optical fiber. Since the optical fiber is available with a diameter of the order of 10 μm, a member to be flaw-detected can be detected for a flaw in the order of μm.

BRIEF DESCRIPTION OF THE DRAWINGS

For a more complete understanding of the present invention and the advantages thereof, reference is now made to the following descriptions in conjunction with the accompanying drawings.

DETAILED DESCRIPTION OF THE INVENTION

Embodiments of the present invention will now be described in detail with reference to the accompanying drawings.

First Embodiment

Figure 1:
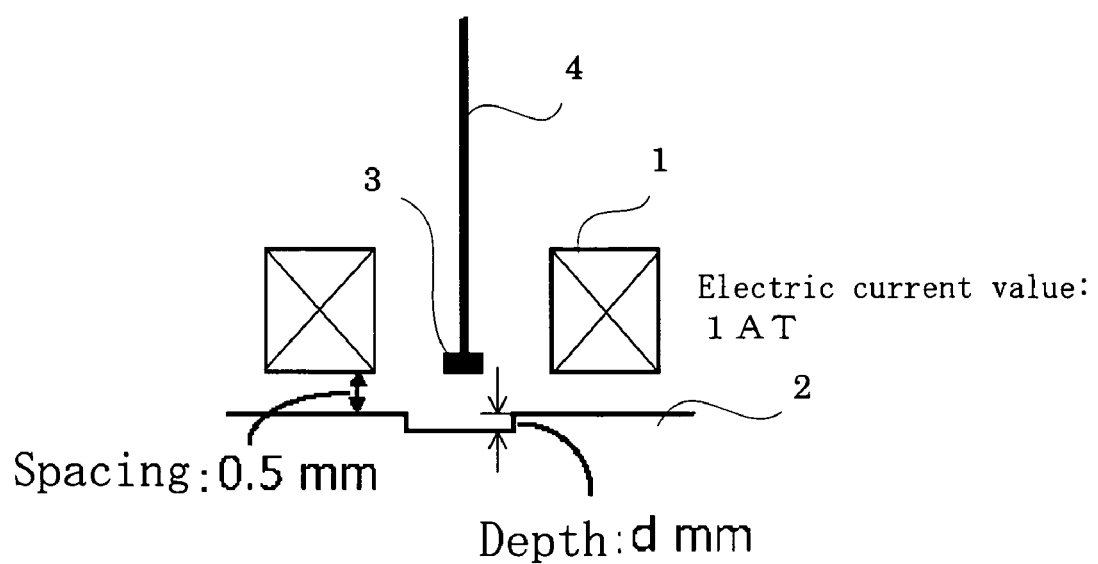
FIG. 1 is an explanatory drawing conceptually showing the relationship among a coil generating a magnetic field, a member to be flaw-detected, and a flaw when calculating this relationship.
Figure 2:
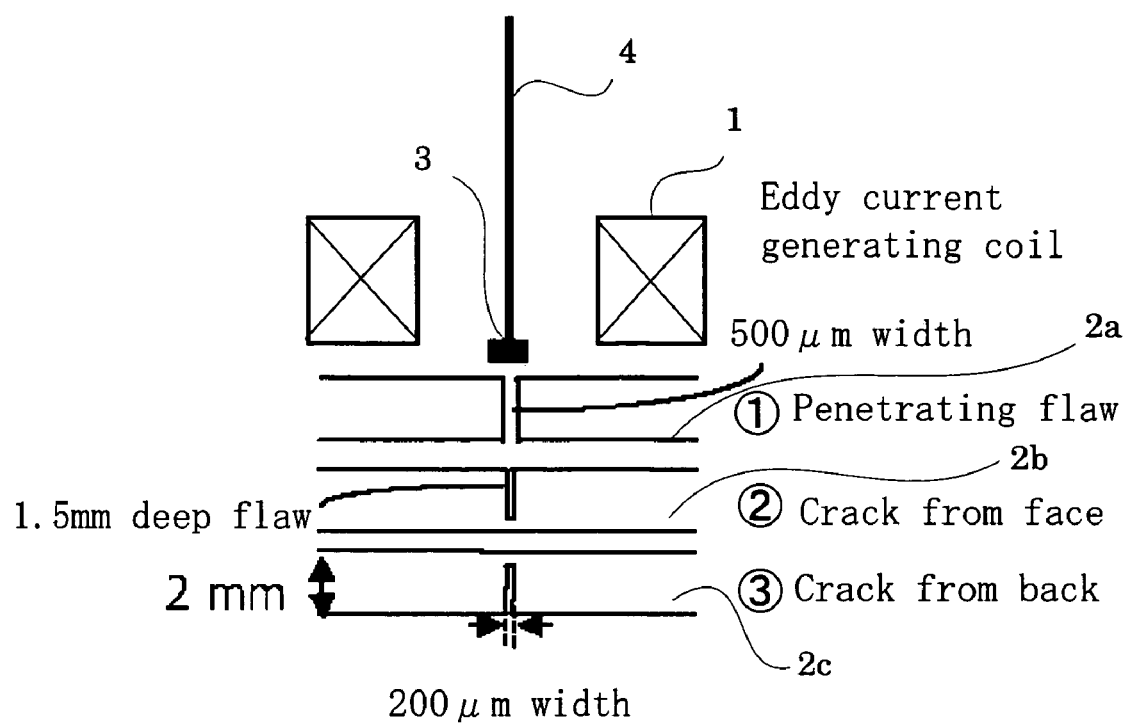
FIG. 2 is an explanatory drawing conceptually showing the manner of flaw detection for various types of flaws formed in the members to be flaw-detected.
Figure 3:
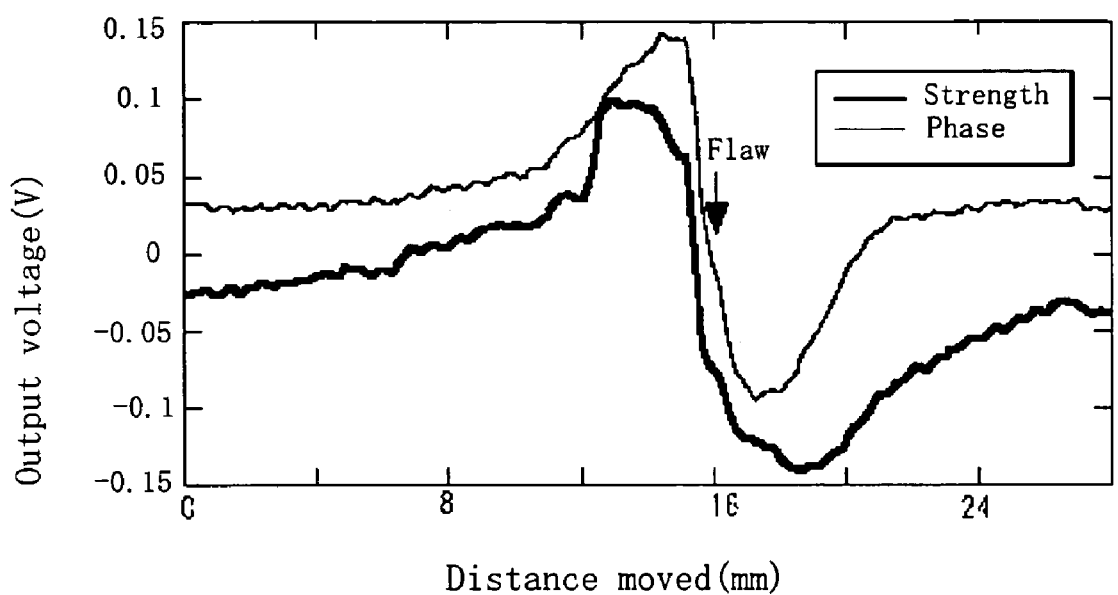
FIG. 3 is a characteristic view showing the results of flaw detection performed for the member to be flaw-detected, the member having a penetrating flaw.
Figure 4:
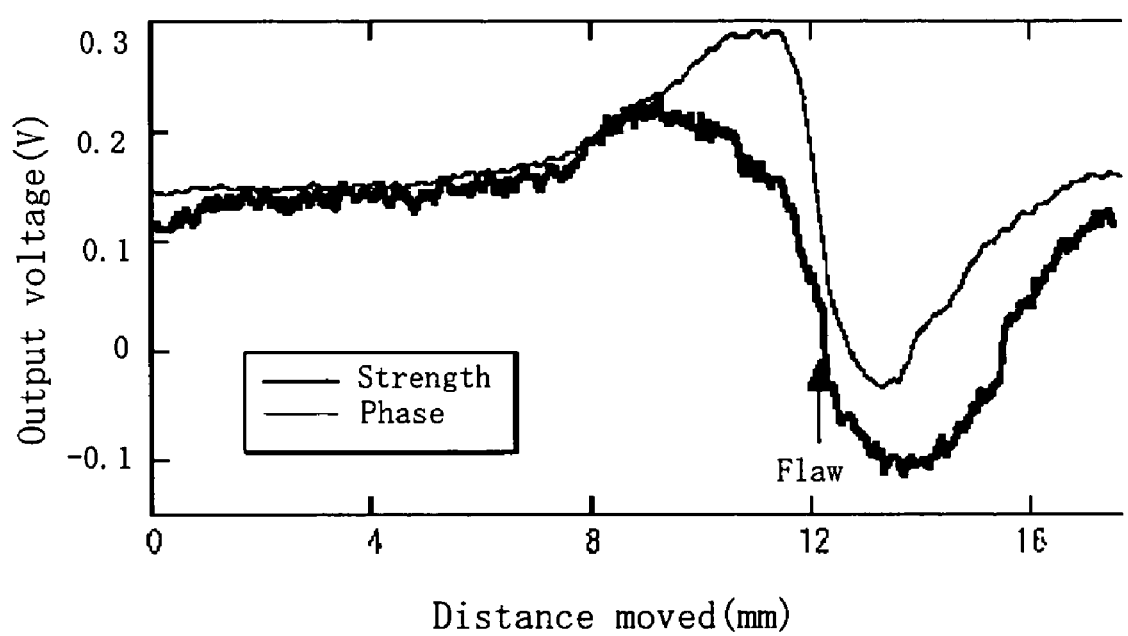
FIG. 4 is a characteristic view showing the results of flaw detection performed for the member to be flaw-detected, the member having a crack in the face thereof.
Figure 5:
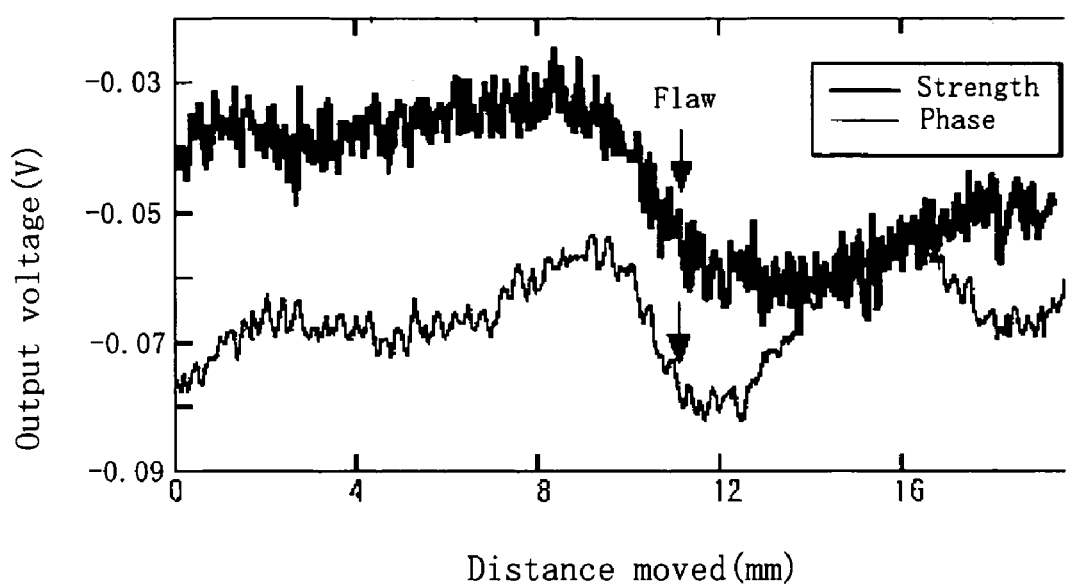
FIG. 5 is a characteristic view showing the results of flaw detection performed for the member to be flaw-detected, the member having a crack in the back thereof.
Figure 6:
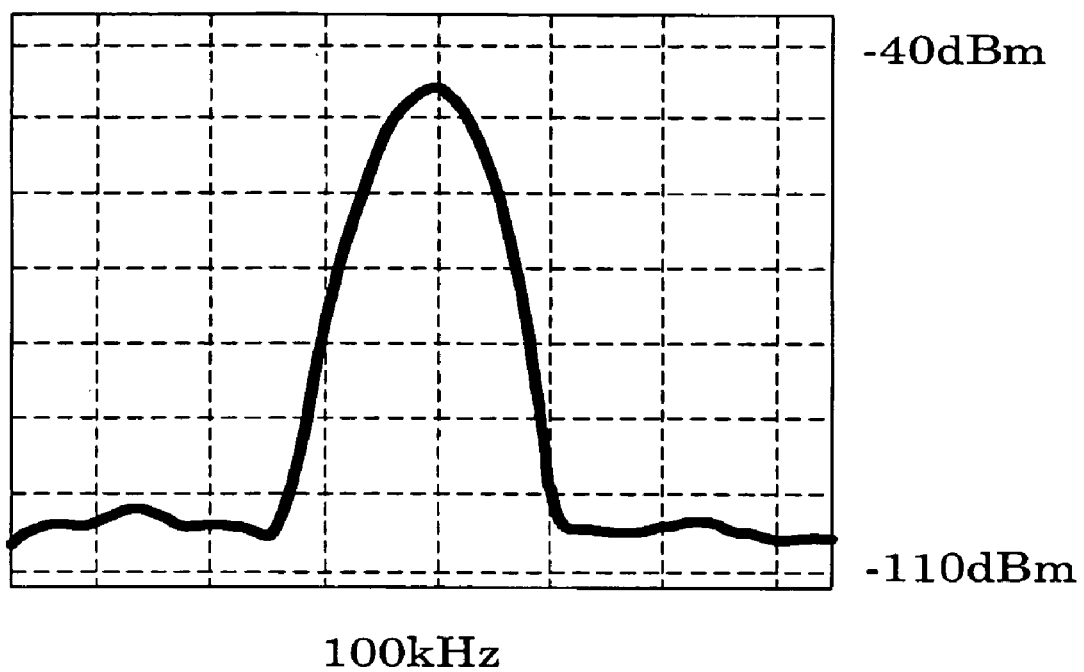
FIG. 6 is a view showing characteristics obtained by generating a magnetic field in the member to be flaw-detected, which is flaw-free, by the coil, and investigating a measurable magnetic field, as a study of the sensitivity of a magneto-optical element.
Figure 7:
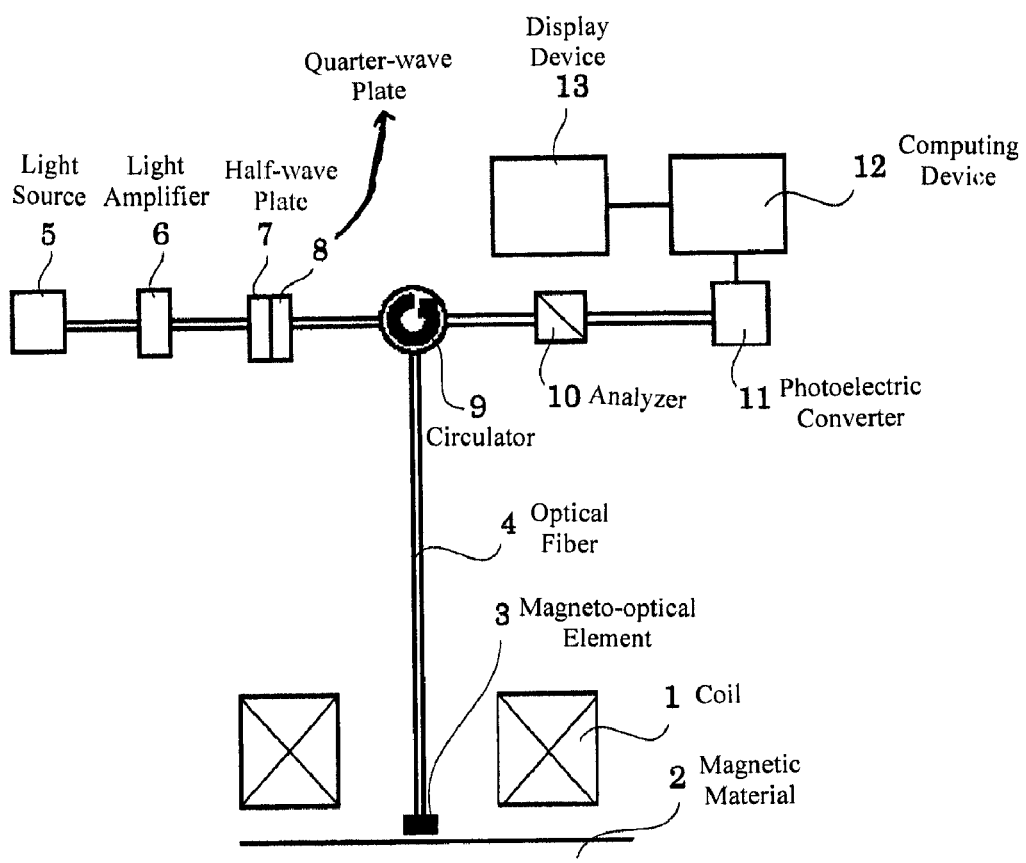
FIG. 7 is an explanatory drawing conceptually showing a flaw detection apparatus according to a first embodiment of the present invention.

FIG. 7 is an explanatory drawing conceptually showing a flaw detection apparatus according to a first embodiment of the present invention. As shown in this drawing, a coil 1 generates an alternating magnetic field for flowing eddy currents in a member 2 to be flaw-detected, which is a magnetic material. As this coil 1, that having an inner diameter of 0.5 to 20 mm, a frequency of an applied voltage of 1 kHz to 5 MHz, and an applied magnetic flux density of 1 to 100 G, for example, is used.

A magneto-optical element 3 is disposed at the center of an inner peripheral portion of the coil 1 so as to have a reflective film at the end face thereof opposed to the face of the member 2 to be flaw-detected, and to be placed in the magnetic field generated by the coil 1. The magneto-optical element 3 is adapted to allow incident light to enter via an optical fiber 4 and deliver it as reflected light via the optical fiber 4, with the plane of polarization of the incident light being rotated. That is, the incident light has a plane of polarization rotated in accordance with the strength of the magnetic field by Faraday effect. Thus, a flaw detection signal, which represents a change in a magnetic flux due to a flaw in the member 2 to be flaw-detected, can be formed based on the rotation angle of the plane of polarization in the reflected light.

A single-mode optical fiber can be preferably applied as the optical fiber 4. More preferably, it is TEC Optical Fiber (trade name) which is the single-mode optical fiber increased in the core diameter of an end portion thereof. This is because the TEC Optical Fiber has a small numerical aperture (NA) and, accordingly, enables the reflected light to be entered with good efficiency. The magneto-optical element 3 can be prepared by the floating zone method or liquid phase epitaxy. The following compositions, for example, are used:

$$A_{3-x}Ce_xFe_{5-y}B_yO_{12}$$

$$A_{3-x}Bi_xFe_{5-y}B_yO_{12}$$

where A represents a rare earth element, B represents an element of group 13, and the composition ratios x and y are in the following ranges:

x=0 to 3 y=0 to 3

Figure 8:
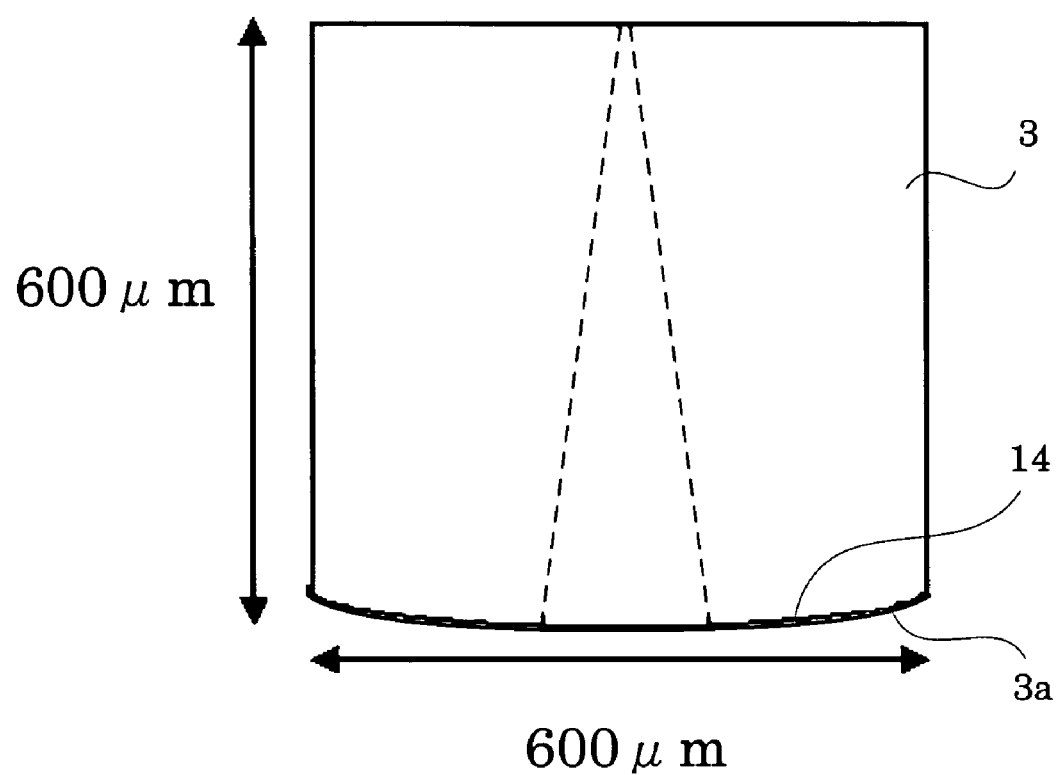
FIG. 8 is an enlarged view showing details of the configuration of a magneto-optical element extracted from FIG. 7.

An end face 3a of the magneto-optical element 3 has the reflecting surface of a reflective film 14 as a curved surface so that the reflected light will be converged on the incident end plane of the optical fiber 4, as shown in FIG. 8. The reflective film 14 can be preferably formed from a metal film (for example, gold) or a dielectric multi-layered film ($SiO_2/Ta_2O_5$ multi-layered film).

By so forming the end face 3a into a curved surface, the reflected light is converged on the optical fiber. For example, when a crystal of the magneto-optical element 3 of 600 μm square is connected to TEC Optical Fiber (trade name) having a core diameter of 30 μm and NA of 0.033, the optical path width increases by 8.9 μm during a one-way travel, so that the reflected light is converged by providing a curved surface of 1.01 mm in diameter.

A light source 5 generates light for flaw detection and, for example, can be preferably composed of a laser diode having a wavelength of 1.55, 1.3 or 0.8 μm and an output of 1 to 4 mW.

A light amplifier 6 amplifies the light emitted by the light source 5, and may be provided, if necessary. A λ/2 plate 7, and a λ/4 plate 8 adjust the polarized state of light to be transmitted by the optical fiber 4. These plates 7 and 8 are designed to adjust the polarized state disturbed by various causes during transmission through the optical fiber 4, for example, vibrations of the optical fiber 4, thereby converting the light incident on an analyzer 10 into linearly polarized light.

A circulator 9 guides the light from the light source 5 toward the magneto-optical element 3, and guides the reflected light reflected by the magneto-optical element 3 toward the analyzer 10. Thus, as in the present embodiment, the circulator 9 is interposed midway through the optical path, whereby the optical path can concurrently serve as the optical path for entry of light into the magneto-optical element 3, and the optical path for leading the light reflected by the magneto-optical element 3. That is, a single optical fiber 4 suffices.

Figure 9:
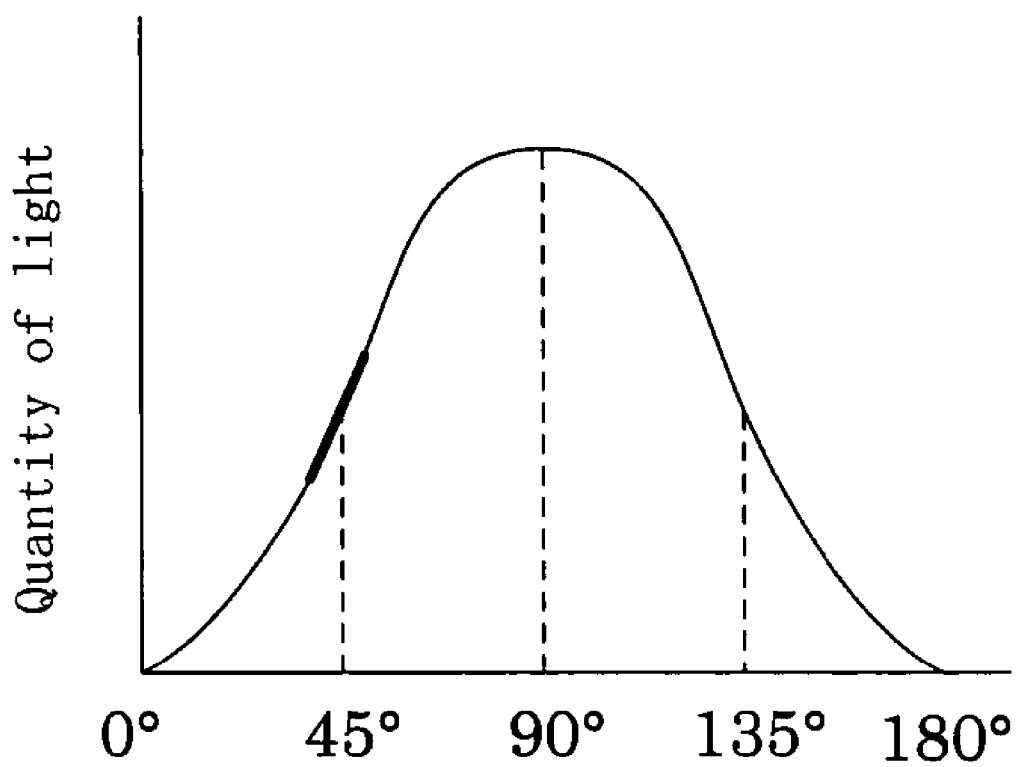
FIG. 9 is a characteristic view showing the characteristics of an analyzer of FIG. 7.

The analyzer 10 is set at an angle at which a change in the magnetic flux density due to a flaw in the member 2 to be flaw-detected becomes maximal (i.e., the angle is set at 45 degrees with respect to transmitted light). That is, as shown in FIG. 9, when the member 2 to be flaw-detected is free of a flaw, the angle is 45 degrees, and the analyzer 10 is adjusted to utilize a straight-line portion centered around the 45 degrees.

A photoelectric conversion element 11 converts the light, which has-passed through the analyzer 10, into an electric signal representing the intensity of the light, and can be preferably composed of a photodiode.

A computing device 12 processes the output signal of the photoelectric conversion element 11 to detect the flaw in the member 2 to be flaw-detected, based on the rotation angle of the plane of polarization of the reflected light. Various concrete configurations can be thought of as the computing device 12, which, however, may be one having, at least, the function of a spectrum analyzer or a lock-in amplifier for detecting the level of the signal having a particular frequency. Data, such as the properties of the flaw and the depth of the flaw, can be obtained by constructing a database on the properties of various flaws (a penetrating flaw, a crack from the face, a crack from the back, etc.), and a database representing the correlation between the depth of the flaw and the signal level, and consulting these databases when processing the aforementioned signal.

A display device 13 visualizes and displays data processed by the computing device 12. The displayed data include, for example, the position and shape of the flaw.

In such a flaw detection apparatus, light which has exited from the light source 5 is incident on the magneto-optical element 3 via the light amplifier 6, λ/2 plate 7, λ/4 plate 8, and circulator 9, and is reflected by the reflective film 14 (see FIG. 8) of the magneto-optical element 3 to arrive at the analyzer 10. At this time, polarized light which passes through the analyzer 10 is influenced by the magnetic field where the magneto-optical element 3 is placed. Under this influence, its plane of polarization rotates in accordance with the magnetic flux density. Thus, when the magnetic field is disturbed by the flaw of the member 2 to be flaw-detected, it is reflected as a change in the rotation angle of the plane of polarization. As a result, the electric signal, which is obtained by converting the output light of the analyzer 10 by the photoelectric conversion element 11, becomes a signal including information on the flaw of the member 2 to be flaw-detected. By properly processing this electrical signal, information on flaw detection can be obtained.

At this time, resolution for flaw detection depends on the core diameter of the optical fiber 4. That is, the resolution can be reduced to the order of μm.

Second Embodiment

Figure 10:
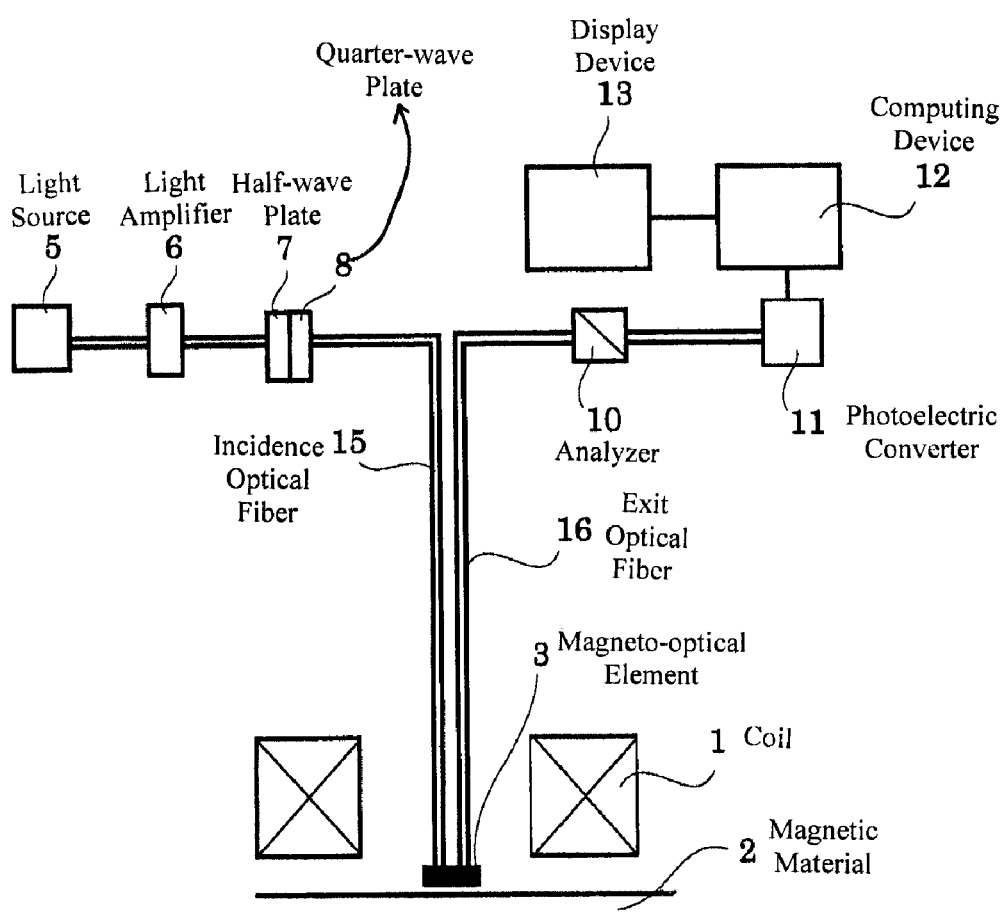
FIG. 10 is an explanatory drawing conceptually showing a flaw detection apparatus according to a second embodiment of the present invention.

FIG. 10 is an explanatory drawing conceptually showing a flaw detection apparatus according to a second embodiment of the present invention. As shown in the drawing, the flaw detection apparatus according to the present embodiment has an incidence optical fiber 15 and an exit optical fiber 16 provided independently. Thus, the circulator 9 (see FIG. 7) is unnecessary.

Other features are the same as those in the first embodiment shown in FIG. 7. Thus, the same portions as those in the first embodiment will be assigned the same numerals as those in the first embodiment, and duplicate explanation omitted.

According to the present embodiment, the same actions and effects as those in the first embodiment can be obtained, with the only difference existing in the optical path of incident light into and the optical path of exit light from the magneto-optical element 3.

Third Embodiment

Figure 11:
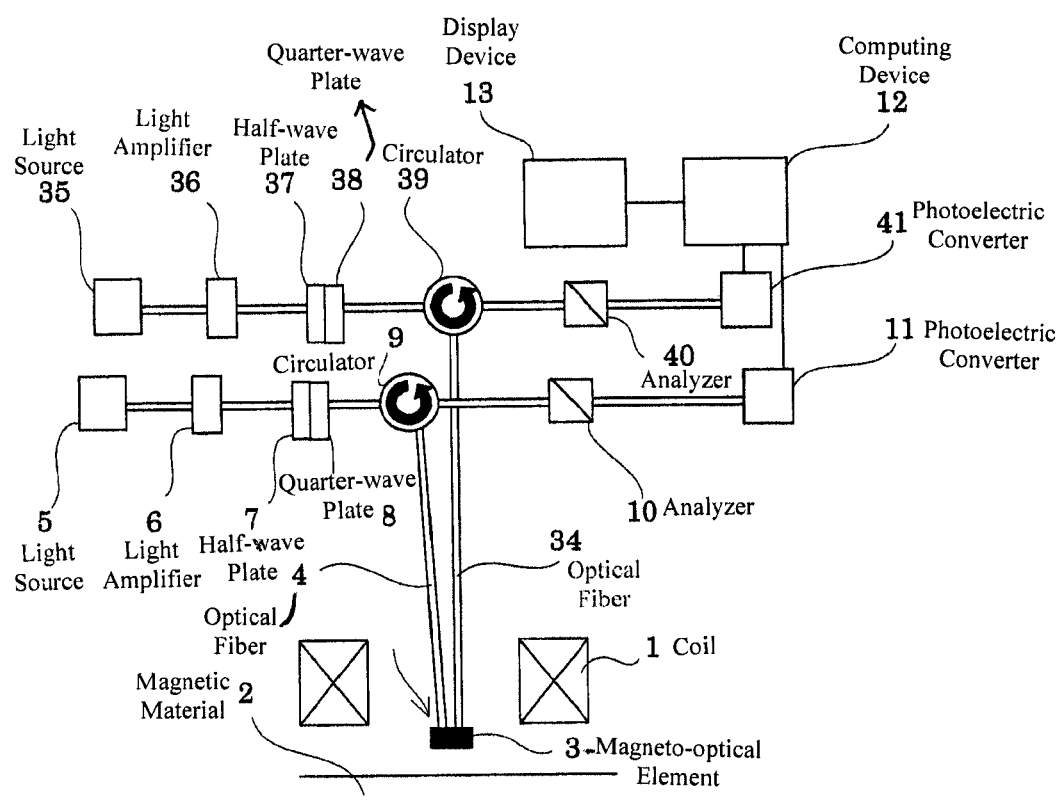
FIG. 11 is an explanatory drawing conceptually showing a flaw detection apparatus according to a third embodiment of the present invention which comprises a plurality of optical systems combined with one coil.

FIG. 11 is an explanatory drawing conceptually showing a flaw detection apparatus according to a third embodiment of the present invention. As shown in the drawing, the flaw detection apparatus according to the present embodiment detects magnetic flux densities at two different points of a magneto-optical element 3 by two optical systems of the same configuration. That is, the flaw detection apparatus has a light source 35, a light amplifier 36, a λ/2 plate 37, a λ/4 plate 38, a circulator 39, an optical fiber 34, an analyzer 40 and a photoelectric conversion element 41, which constitute an optical system of the same configuration as that constituted by the light source 5, light amplifier 6, λ/2 plate 7, λ/4 plate 8, circulator 9, optical fiber 4, analyzer 10 and photoelectric conversion element 11 shown in FIG. 7, and feeds reflected light reflected by two different points of the magneto-optical element 3 to a computing device 12.

Other features are the same as those in the first embodiment shown in FIG. 7. Thus, the same portions as those in the first embodiment will be assigned the same numerals as those in the first embodiment, and duplicate explanations omitted.

Figure 12:
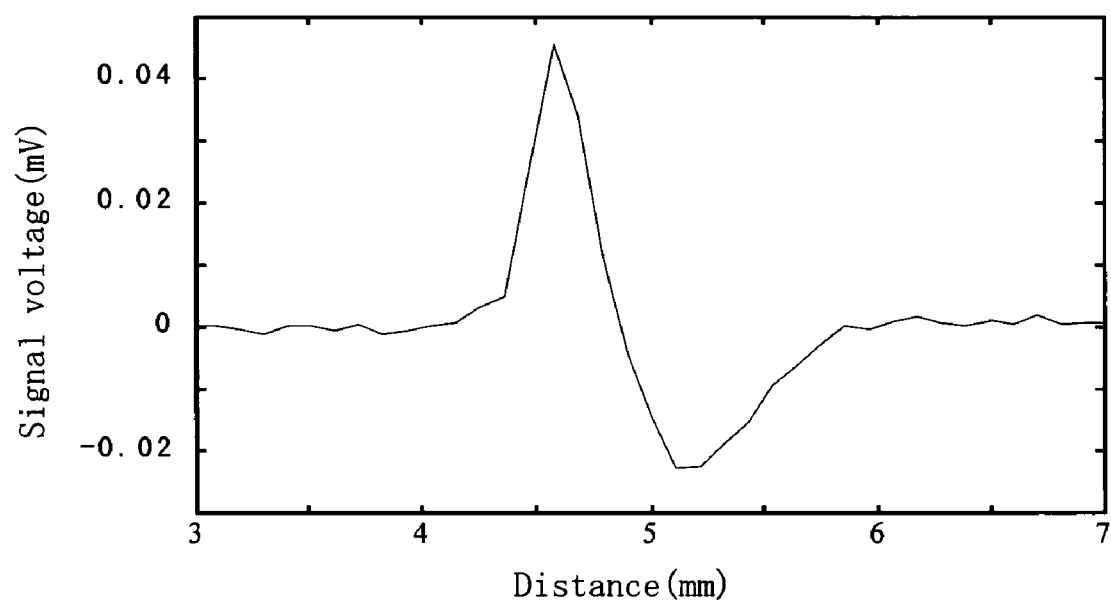
FIG. 12 is a characteristic view showing the results of measurement obtained by the third embodiment of the present invention.

According to the present embodiment, a change in the magnetic flux density due to the state of a member 2 to be flaw-detected (see FIG. 11) can be detected, as shown, for example, in FIG. 12, with the use of the two different sites of the same magneto-optical element 3. That is, a disturbance in the magnetic field at the same location of the member 2 to be flaw-detected can be detected at the two different positions of the magneto-optical element 3 by moving the position of the same magneto-optical element 3 relative to the member 2 to be flaw-detected. Then, a characteristic view based on the difference between the detected values at both positions is obtained. It is possible to detect, accurately, the width of the flaw by the distance between the peaks of the characteristics shown in FIG. 12, and the location of the flaw by the position of the midpoint between the peaks. The accuracy of detection in this case increases, without doubt, compared with the first embodiment shown in FIG. 7. The reason is that in the case of the first embodiment, detection is performed based on one peak of the characteristics, thus resulting in a value in a wider range than in the present embodiment, particularly if the change rate in the vicinity of the peak is small.

Moreover, the detected value obtained by the other optical system based on detection at the same location is subtracted from the peak value of the characteristics detected by one of the optical systems, whereby noise components can be removed, and a precise peak value can be obtained. Thus, the depth of the flaw based on the peak value can be detected accurately.

Other Embodiment

In the third embodiment shown in FIG. 11, the same optical system as the optical system in the first embodiment shown in FIG. 7 is provided as an additional optical system. However, there may be conceived an embodiment involving two of the optical systems in the second embodiment shown in FIG. 10. In this embodiment as well, the same actions and effects as those in the third embodiment can be exhibited.

EXAMPLES

In each of the above embodiments, the single coil 1 and the single magneto-optical element 3 are used, and the magneto-optical element 3 is disposed to be located at the center of the inner periphery of the coil 1. However, various modes can be conceived in connection with the relative positional relationship between the coil 1 and the magneto-optical element 3, and the numbers of the coil 1 and the magneto-optical element 3. Thus, several representative modes will be described as Examples.

First Example

Figure 13:
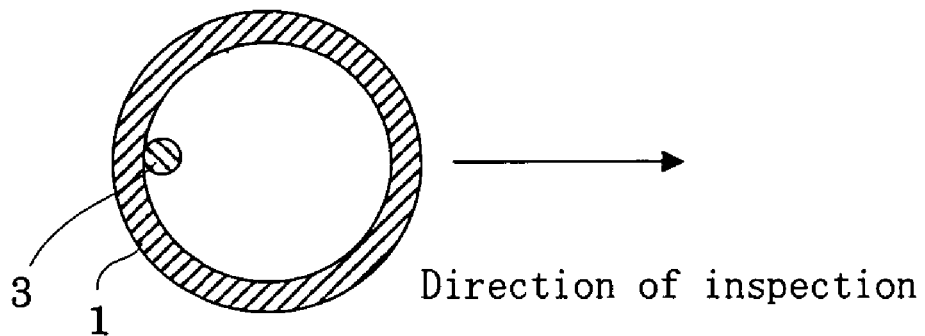
FIG. 13 is an explanatory drawing showing the relationship between the magneto-optical element and the coil according to a first example of the present invention.

As shown in FIG. 13, the magneto-optical element 3 is disposed in contact with the inner peripheral surface of the coil 1. Since this is the closest position to the coil 1, a relatively great change in the magnetic flux density can be detected. Also, it suffices to adhere the magneto-optical element 3 to the inner peripheral surface of the coil 1. Thus, the magneto-optical element 3 can be easily aligned. Furthermore, the magneto-optical element 3 may be in contact with the outer peripheral surface of the coil 1. In this case, too, the same actions and effects can be obtained. Incidentally, eddy currents due to the coil 1 are the greatest at a site directly below the coil 1, but the magneto-optical element 3 cannot be disposed directly below the coil 1. This is because the coil 1 will be lifted off from the face of the member 2 to be flaw-detected.

Second Example

Figure 14:
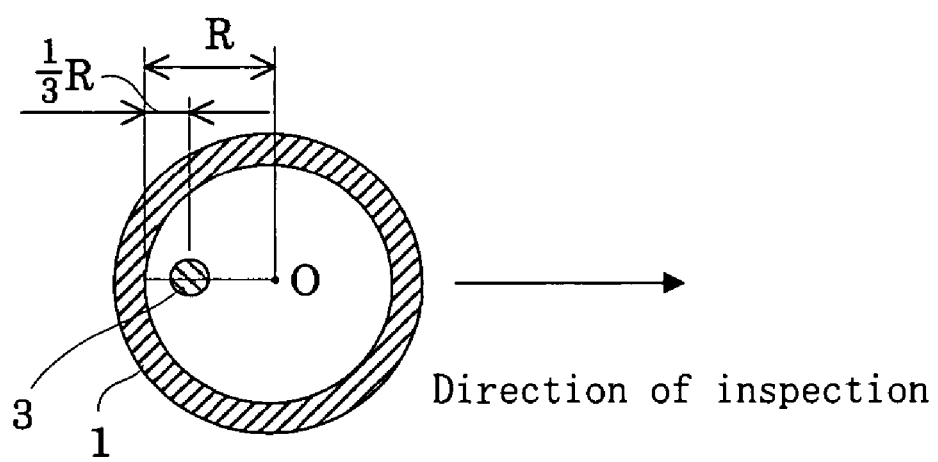
FIG. 14 is an explanatory drawing showing the relationship between the magneto-optical element and the coil according to a second example of the present invention.

As shown in FIG. 14, the magneto-optical element 3 is disposed a third of a distance R spaced from the inner peripheral surface of the coil 1, the distance R being from the inner peripheral surface of the coil 1 to the center O of an inner peripheral portion of the coil 1. Analysis of an electromagnetic field formed by the coil 1 shows that this position of disposition is the position where eddy currents are the greatest, except at a site directly below the coil 1. Accordingly, a change in the magnetic flux density due to the flaw or the like is maximal there. Thus, a satisfactory accuracy of detection can be obtained.

Third Example

Figure 15:
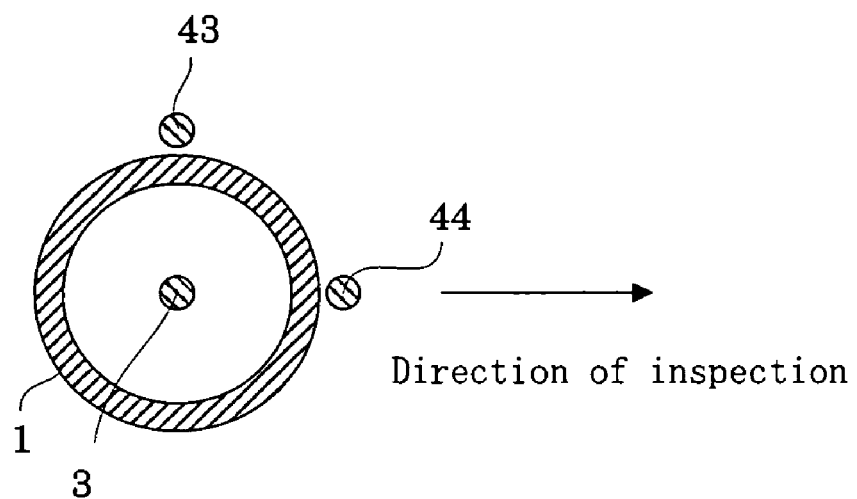
FIG. 15 is an explanatory drawing showing the relationship between the magneto-optical elements and the coil according to a third example of the present invention.

As shown in FIG. 15, magneto-optical elements 43, 44 are disposed, with a phase difference of 90 degrees being provided therebetween, in an outer peripheral portion of the coil 1. In this case, flaw detection at three locations can be carried out simultaneously. Thus, flaw detection, including the direction of extension of the flaw, is possible.

Fourth Example

Figure 16:
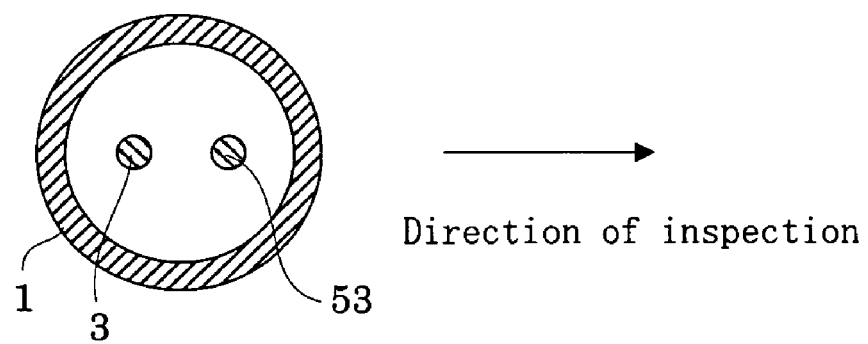
FIG. 16 is an explanatory drawing showing the relationship between the magneto-optical elements and the coil according to a fourth example of the present invention.

As shown in FIG. 16, a plurality of (two in the drawing) magneto-optical elements, 3, 53, may be disposed in an inner peripheral portion of the coil 1 so that flaw detection at a plurality of sites can be performed at the same time. This feature can contribute to an improvement in the efficiency of flaw detection.

Fifth Example

Figure 17:
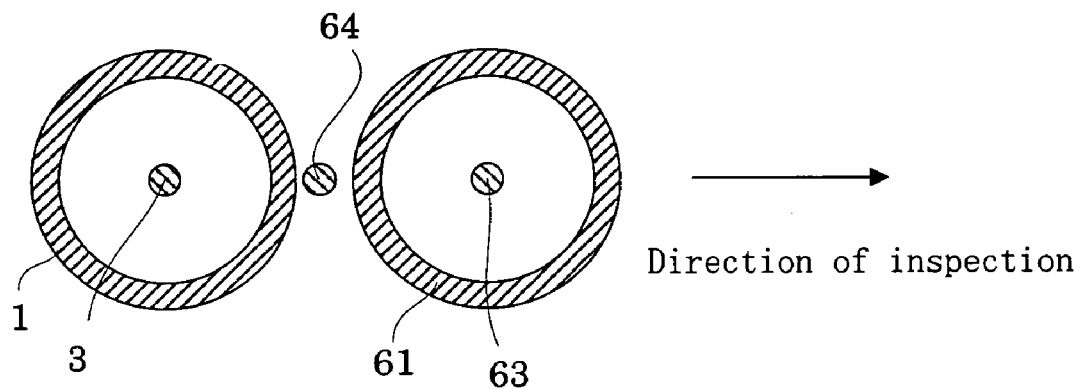
FIG. 17 is an explanatory drawing showing the relationship between the magneto-optical elements and the coils according to a fifth example of the present invention.

As shown in FIG. 17, there are two coils, 1, 61, which have magneto-optical elements 3, 63 in inner peripheral portions thereof, respectively; electric currents in opposite directions are fed to the coils 1, 61 so that magnetic fluxes generated by the coils 1, 61 are superimposed on each other; and another magneto-optical element 64 is disposed between the coil 1 and the other coil 61. Consequently, flaw detection can be performed based on the rotation angle of the plane of polarization due to the superimposed magnetic fluxes.

Sixth Example

Figure 18:
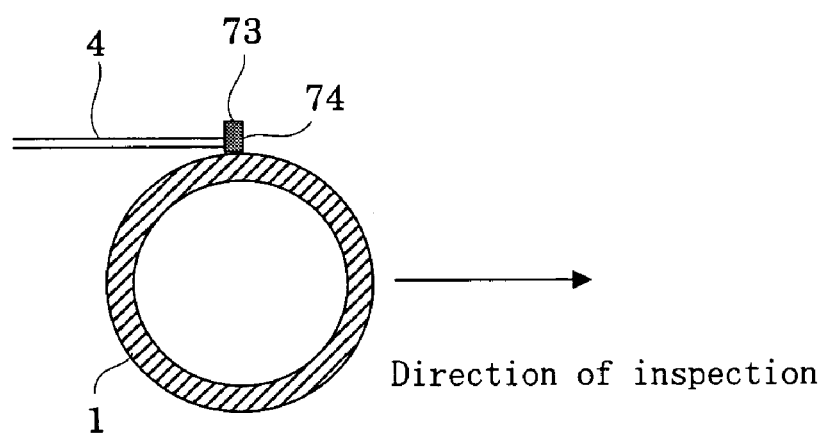
FIG. 18 is an explanatory drawing showing the relationship between the magneto-optical element and the coil according to a sixth example of the present invention.

As shown in FIG. 18, in order that a magneto-optical element 73 can detect a change in a magnetic field of a component in a direction parallel to the face of the member 2 to be flaw-detected (see FIG. 7), light is entered in the parallel direction via an optical fiber 4, and the light is reflected in the parallel direction by a reflective film 74 formed on a surface perpendicular to the parallel direction. According to the present example, only a change in the magnetic flux density of the component parallel to the face of the member 2 to be flaw-detected (see FIG. 7) is detected, so that the presence of the flaw itself can be detected with high accuracy.

Seventh Example

Figure 19:
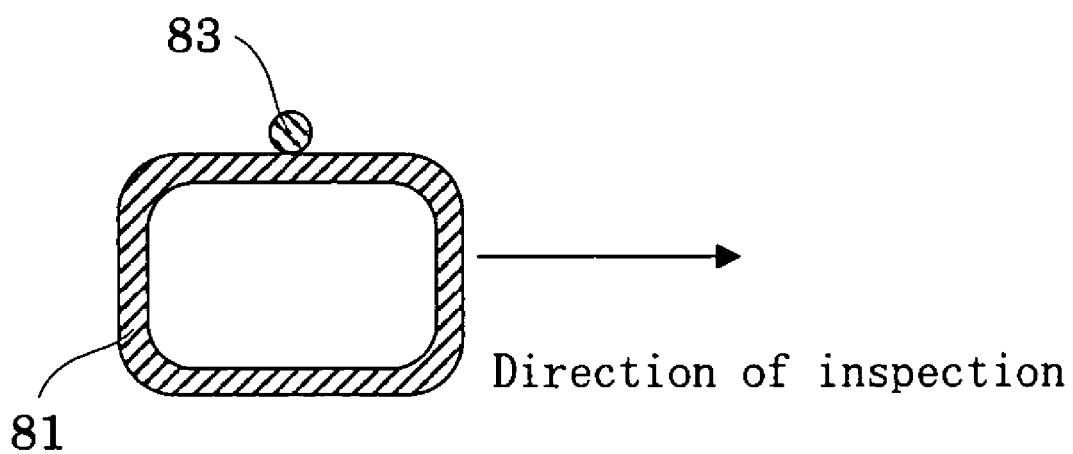
FIG. 19 is an explanatory drawing showing the relationship between the magneto-optical element and the coil according to a seventh example of the present invention.
Figure 20A:
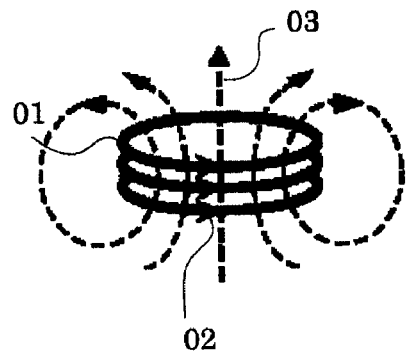
FIGS. 20A to 20D are explanatory drawings showing the principle of the eddy current flaw detection method according to an earlier technology.
Figure 20B:
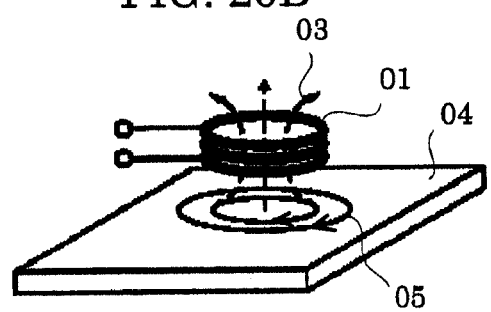
Figure 20C:
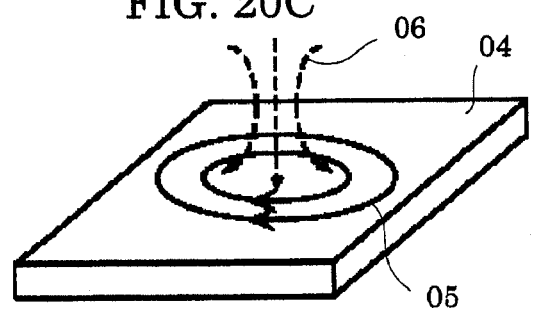
Figure 20D:
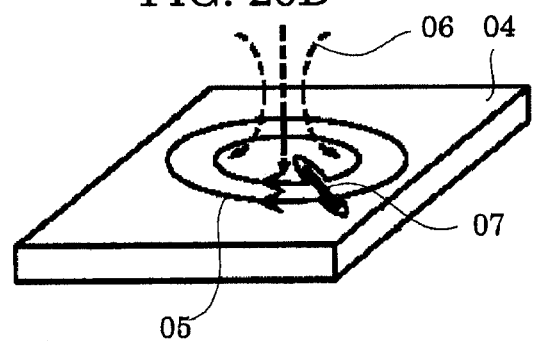
Figure 21:
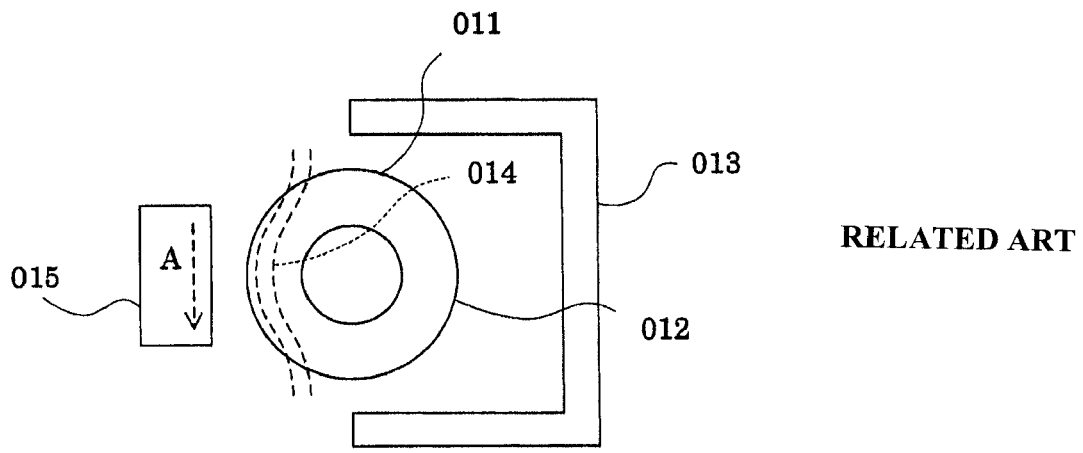
FIG. 21 is an explanatory drawing showing the principle of the flaw detection method according to the earlier technology which detects a change in a magnetic flux density as a change in the rotation angle of the plane of polarization with the use of the Faraday effect.
Figure 22:
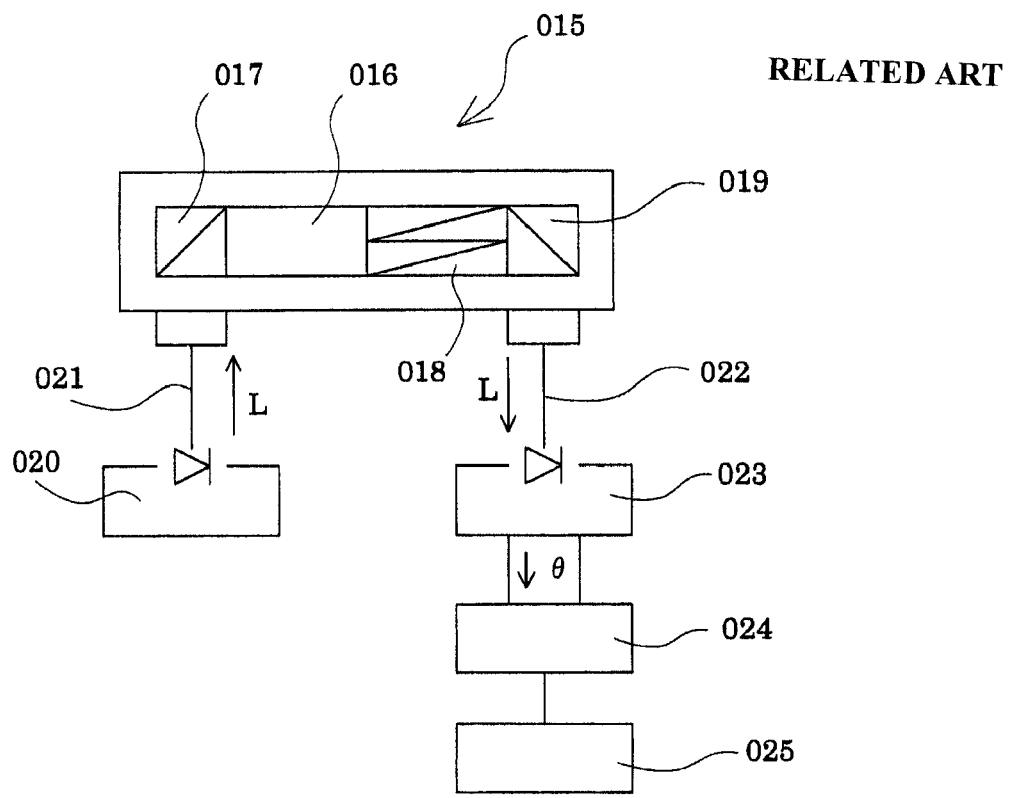
FIG. 22 is a block diagram showing a flaw detection apparatus which actualizes the flaw detection method shown in FIG. 21.

According to the present example, as shown in FIG. 19, a coil 81 is rectangularly shaped, and a magneto-optical element 83 is disposed in proximity to a straight-line portion of the coil 81. In the present example, a magnetic flux density change distribution in the neighborhood of the magneto-optical element 83 can be rendered small to contribute to high-resolution detection.

Each of the above-described examples can be applied not only to the first to second embodiments, but also to the third embodiment. In the third embodiment having the two optical systems, the end faces of the optical fibers 4 and 34 are in contact with the magneto-optical element 3.

The present invention can be effectively used in industrial fields where nondestructive inspection of a member to be flaw-detected, which is formed of a magnetic material, is performed when detecting a flaw on the surface of or in the interior of a metallic material, such as piping, and in industrial fields where testing devices for such purposes are produced.

Although the embodiments and examples of the present invention have been described above, the present invention is not limited to them, but may be varied in many other ways. It should be understood that such changes, substitutions and alterations can be made therein without departing from the spirit and scope of the invention as defined by the appended claims.

What is claimed is:

1. A flaw detection apparatus, comprising:
   a first coil for producing an alternating-current magnetic field for flowing eddy currents in a magnetic material as a member to be flaw-detected;
   a first magneto-optical element disposed in a neighborhood of the first coil and having an end face provided with a reflective film;
   an incidence optical fiber for entering light from a light source into the first magneto-optical element toward the reflective film;
   an exit optical fiber for entering reflected light reflected by the reflective film into an analyzer;
   a photoelectric conversion element for converting output light of the analyzer into an electrical signal; and
   computing means for processing an output signal of the photoelectric conversion element and detecting a flaw of the member to be flaw-detected, based on a rotation angle of a plane of polarization of the reflected light;
   wherein the first magneto-optical element is directly affixed to an end face of the incidence optical fiber and an end face of the exit optical fiber.

2. The flaw detection apparatus according to claim 1, wherein
   the incidence optical fiber and the exit optical fiber are formed of a single optical fiber,
   a circulator is interposed halfway through an optical path of the single optical fiber,
   the light from the light source enters the first magneto-optical element via the circulator, and
   the reflected light from the first magneto-optical element enters the analyzer via the circulator.

3. The flaw detection apparatus according to claim 1, wherein
   a polarizer, which adjusts the output light from the optical fiber to become linearly polarized light at a position of the analyzer, is disposed halfway through the optical path formed of the optical fiber.

4. The flaw detection apparatus according to claim 1, wherein
   the optical fiber is formed of a polarization maintenance fiber.

5. The flaw detection apparatus according to claim 1, wherein
   a reflecting surface formed by the reflective film is rendered as a curved surface so that the reflected light is converged on an end plane of incidence of the exit optical fiber.

6. The flaw detection apparatus according to claim 1, wherein
   the first magneto-optical element is disposed at a center of an inner peripheral portion of the first coil.

7. The flaw detection apparatus according to claim 1, wherein
   the first magneto-optical element is disposed in contact with a circumferential surface of the first coil.

8. The flaw detection apparatus according to claim 1, wherein
   a second magneto-optical element is disposed in an outer peripheral portion of the first coil, so that flaw detection can be performed simultaneously at sites where the first and second magneto-optical elements are disposed.

9. The flaw detection apparatus according to claim 1, wherein
   a second magneto-optical element is disposed in an inner peripheral portion of the first coil, so that flaw detection can be performed simultaneously at sites where the first and second magneto-optical elements are disposed.

10. The flaw detection apparatus according to claim 1, further comprising a second coil, a second magneto-optical element, and a third magneto-optical element; wherein:
    the first magneto-optical element is disposed in an inner peripheral portion of the first coil, the second magneto-optical element is disposed in an inner peripheral portion of the second coil,
    a first electric current in a first direction is fed to the first coil, and a second electric current in a second direction opposite to the first direction is fed to the second coil, so that a first magnetic flux generated by the first coil and a second magnetic flux generated by the second coil are superimposed on each other, and
    the third magneto-optical element is disposed between the first coil and the second coil so that flaw detection can be performed based on a rotation angle of a plane of polarization due to the superimposed magnetic fluxes.

11. The flaw detection apparatus according to claim 1, wherein
    in order that the first magneto-optical element can detect a change in a magnetic field of a component in a direction parallel to a face of the member to be flaw-detected, light is entered in the parallel direction, and the light is reflected in the parallel direction by the reflective film formed on a surface perpendicular to the parallel direction.

12. The flaw detection apparatus according to claim 1, wherein
    the first coil is rectangularly shaped, and the first magneto-optical element is disposed in proximity to a straight-line portion of the first coil.

13. A flaw detection apparatus, comprising:
    a first coil for producing an alternating-current magnetic field for flowing eddy currents in a magnetic material as a member to be flaw-detected;
    a first magneto-optical element disposed in a neighborhood of the first coil and having an end face provided with a reflective film;
    a first incidence optical fiber for entering light from a first light source into the first magneto-optical element toward the reflective film;
    a second incidence optical fiber for entering light from a second light source into the first magneto-optical element toward the reflective film;
    a first exit optical fiber for entering a first reflected light reflected by the reflective film into a first analyzer;
    a second exit optical fiber for entering a second reflected light reflected by the reflective film into a second analyzer;
    a first photoelectric conversion element for converting a first output light of the first analyzer into a first electrical signal; a second photoelectric conversion element for converting a second output light of the second analyzer into a second electrical signal; and computing means for processing a first output signal of the first photoelectric conversion element and a second output signal of the second photoelectric conversion element, and detecting a flaw of the member to be flaw-detected based on rotation angles of planes of polarization of the first reflected light and the second reflected light;

wherein the first magneto-optical element is directly affixed to an end face of the first incidence optical fiber, an end face of the second incidence fiber, an end face of the first exit optical fiber, and an end face of the second exit optical fiber.

14. The flaw detection apparatus according to claim 13, wherein the first incidence optical fiber and the first exit optical fiber are formed of a first single optical fiber, the second incidence optical fiber and the second exit optical fiber are formed of a second single optical fiber, a first circulator is interposed halfway through an optical path of the first single optical fiber, a second circulator is interposed halfway through an optical path of the second single optical fiber, the light from the first light source enters the first magneto-optical element via the first circulator, the light from the second light source enters the first magneto-optical element via the second circulator, the first reflected light from the first magneto-optical element enters the first analyzer via the first circulator, and the second reflected light from the first magneto-optical element enters the second analyzer via the second circulator.

15. The flaw detection apparatus according to claim 13, further comprising:

a first polarizer, which adjusts the first reflected light to become linearly polarized light at a position of the first analyzer, and which is disposed halfway through the optical path of the first single optical fiber; and a second polarizer, which adjusts the second reflected light to become linearly polarized light at a position of the second analyzer, and which is disposed halfway through the optical path of the second single optical fiber.

16. The flaw detection apparatus according to claim 13, wherein each of the optical fibers is formed of a polarization maintenance fiber.

17. The flaw detection apparatus according to claim 13, wherein a reflecting surface formed by the reflective film is rendered a curved surface so that the first reflected light is converged on an end plane of incidence of the first exit optical fiber, and the second reflected light is converged on an end plane of incidence of the second exit optical fiber.

18. The flaw detection apparatus according to claim 13, wherein the first magneto-optical element is disposed at a center of an inner peripheral portion of the first coil.

19. The flaw detection apparatus according to claim 13, wherein the first magneto-optical element is disposed in contact with a circumferential surface of the first coil.

20. The flaw detection apparatus according to claim 13, wherein a plurality of second magneto-optical elements are disposed in an outer peripheral portion of the first coil so that flaw detection can be performed simultaneously at sites where the first and second magneto-optical elements are disposed.

21. The flaw detection apparatus according to claim 13, wherein a plurality of second magneto-optical elements are disposed in an inner peripheral portion of the first coil so that flaw detection can be performed simultaneously at sites where the first and second magneto-optical elements are disposed.

22. The flaw detection apparatus according to claim 13, further comprising a second coil, a second magneto-optical element, and a third magneto-optical element; wherein:

the first magneto-optical element is disposed in an inner peripheral portion of the first coil, the second magneto-optical element is disposed in an inner peripheral portion of the second coil, a first electric current in a first direction is fed to the first coil, and a second electric current in a second direction opposite to the first direction is fed to the second coil, so that a first magnetic flux generated by the first coil and a second magnetic flux generated by the second coil are superimposed on each other, and the third magneto-optical element is disposed between the first coil and the second coil so that flaw detection can be performed based on a rotation angle of a plane of polarization due to the superimposed magnetic fluxes.

23. The flaw detection apparatus according to claim 13, wherein in order that the first magneto-optical element can detect a change in a magnetic field of a component in a direction parallel to a face of the member to be flaw-detected, light is entered in the parallel direction, and the light is reflected in the parallel direction by the reflective film formed on a surface perpendicular to the parallel direction.

24. The flaw detection apparatus according to claim 13, wherein the first coil is rectangularly shaped, and the first magneto-optical element is disposed in proximity to a straight-line portion of the first coil.

25. A flaw detection apparatus, comprising:

a first coil for producing an alternating-current magnetic field for flowing eddy currents in a magnetic material as a member to be flaw-detected;

a first magneto-optical element disposed in a neighborhood of the first coil and having an end face provided with a reflective film;

an incidence optical fiber for entering light from a light source into the first magneto-optical element toward the reflective film;

an exit optical fiber for entering reflected light reflected by the reflective film into an analyzer;

a photoelectric conversion element for converting output light of the analyzer into an electrical signal; and computing means for processing an output signal of the photoelectric conversion element and detecting a flaw of the member to be flaw-detected, based on a rotation angle of a plane of polarization of the reflected light, wherein wherein the first magneto-optical element is directly affixed to an end face of the incidence optical fiber and an end face of the exit optical fiber, and the first magneto-optical element is disposed a third of a distance spaced from an inner peripheral surface of the first coil, the distance being from the inner peripheral surface of the first coil to a center of an inner peripheral portion of the first coil.

26. A flaw detection apparatus, comprising:

a first coil for producing an alternating-current magnetic field for flowing eddy currents in a magnetic material as a member to be flaw-detected;

a first magneto-optical element disposed in a neighborhood of the first coil and having an end face provided with a reflective film;

a first incidence optical fiber for entering light from a first light source into the first magneto-optical element toward the reflective film;

a second incidence optical fiber for entering light from a second light source into the first magneto-optical element toward the reflective film;

a first exit optical fiber for entering a first reflected light reflected by the reflective film into a first analyzer;

a second exit optical fiber for entering a second reflected light reflected by the reflective film into a second analyzer;

a first photoelectric conversion element for converting a first output light of the first analyzer into a first electrical signal; a second photoelectric conversion element for converting a second output light of the second analyzer into a second electrical signal; and computing means for processing a first output signal of the first photoelectric conversion element and a second output signal of the second photoelectric conversion element, and detecting a flaw of the member to be flaw-detected based on rotation angles of planes of polarization of the first reflected light and the second reflected light, wherein wherein the first magneto-optical element is directly affixed to an end face of the incidence optical fiber and an end face of the exit optical fiber, and the first magneto-optical element is disposed a third of a distance spaced from an inner peripheral surface of the first coil, the distance being from the inner peripheral surface of the first coil to a center of an inner peripheral portion of the first coil.

* * * * *